United States Patent [19]

Wang et al.

[11] Patent Number: 4,757,814
[45] Date of Patent: Jul. 19, 1988

[54] PROPORTIONAL CONTROL FOR PNEUMATIC CUTTING DEVICE

[75] Inventors: Carl C. T. Wang, Piedmont; Wayne W. Rogers, Napa; Donald A. Parker, Berkeley, all of Calif.

[73] Assignee: Alcon Laboratories, Inc., Fort Worth, Tex.

[21] Appl. No.: 1,235

[22] Filed: Jan. 7, 1987

Related U.S. Application Data

[63] Continuation of Ser. No. 706,653, Feb. 28, 1985, abandoned.

[51] Int. Cl.⁴ .............................................. A61B 17/32
[52] U.S. Cl. ..................................... 128/318; 128/305
[58] Field of Search ..................... 128/305, 312, 318; 433/101; 137/903

[56] References Cited

U.S. PATENT DOCUMENTS

| 3,399,677 | 9/1968 | Gould et al. | 137/903 |
| 3,752,161 | 8/1973 | Bent | 128/312 |
| 3,842,839 | 10/1974 | Malis et al. | 128/318 |
| 3,899,829 | 8/1975 | Storm et al. | 128/318 |
| 3,977,425 | 8/1976 | Hayashida | 137/903 |
| 4,245,815 | 1/1981 | Willis | 137/903 |
| 4,354,838 | 10/1982 | Hoyer et al. | 433/101 |
| 4,530,357 | 7/1985 | Pawloski | 128/312 |

OTHER PUBLICATIONS

Storz Micro Vit Vitrectomy System Brochure.
Stortz IAS System Brochure.
Storz Micro Vit Vitrectomy System Instruction Manual.

Primary Examiner—Robert P. Swiatek
Assistant Examiner—Cary E. Stone
Attorney, Agent, or Firm—Zarley, McKee, Thomte, Voorhees & Sease

[57] ABSTRACT

A system 10 for proportional control of a pneumatic cutting device 13 includes a linear solenoid valve 11 having a flow rate therethrough proportional to the current passing through the solenoid 32. The linear solenoid valve 11 is actuated by a selectively varied electrical signal generated by a power supply 18 and controlled by a potentiometer 14 which is itself operated by a pedal foot controller 16. Regulated fluid pressure is fed through the linear soleoid valve 11 to a pneumatic cutting device 13 such as an intraocular microscissors which closes increasingly as the applied pressure increases. The linear solenoid valve 11 includes a flow path which is variably constricted or closed by a valve member 36, and a solenoid 32 which is arranged to pull the valve member 36 to open the flow path. An elastic member 35 is disposed to resiliently bias the valve member to the closed position; the linear restoring force of the elastic member provides a generally linear relationship between the fluid flow-through rate and the current through the solenoid 32, and a proportional relationship between the control pedal position and closure of the cutting device.

14 Claims, 1 Drawing Sheet

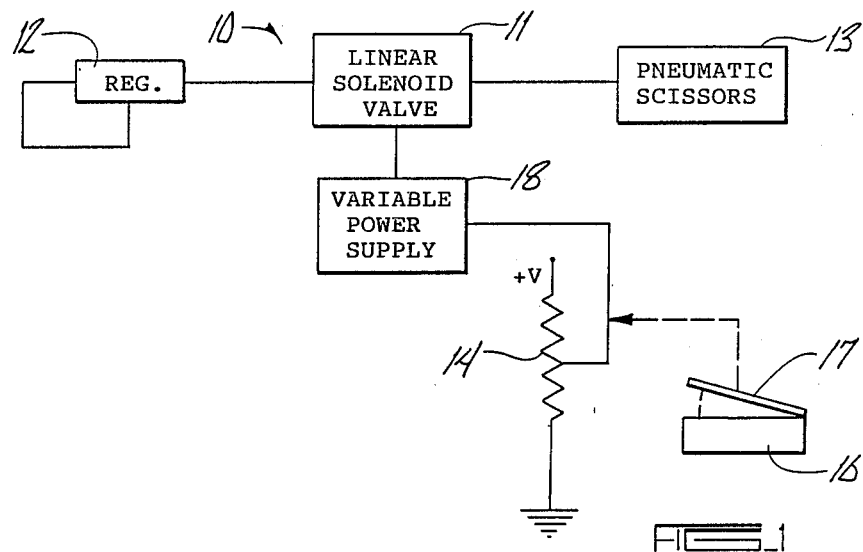
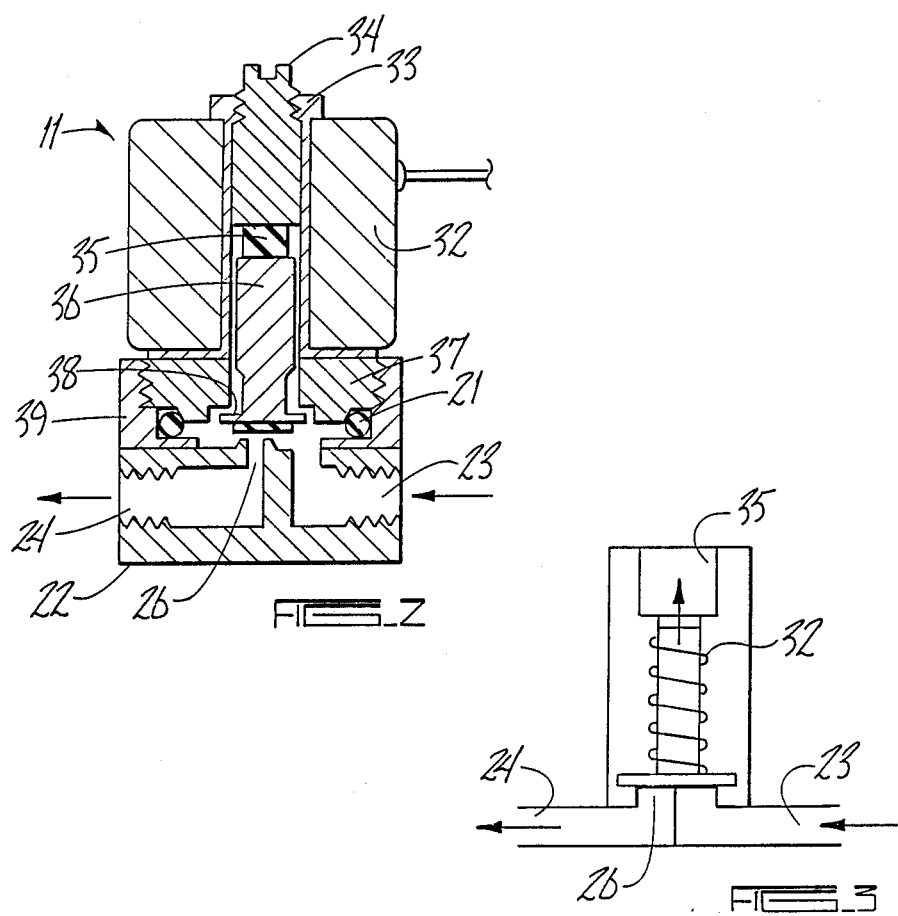

PROPORTIONAL CONTROL FOR PNEUMATIC CUTTING DEVICE

This is a continuation of co-pending application Ser. No. 706,653 filed on Feb. 28, 1985, now abandoned.

BACKGROUND OF THE INVENTION

In the field of surgery, and in particular ophthalmic surgery, there are known in the prior art many cutting instruments which are operated by electrical or pneumatic power. These devices are advantageous in that they increase the cutting rate and cutting force which the surgeon may wield. In addition, they generally allow the surgeon to perform delicate procedures more easily, in that the cutting instrument may be held steady without requiring manual or digital action to effect the cutting action.

One such device is a pneumatic scissors handpiece, otherwise termed an intraocular microscissors. In these devices a piston driven by pneumatic pulses is adapted to drive the scissor blades to open and close rapidly and repeatedly. Although this device is extremely useful, it does have serious drawbacks. One major failing is that the piston action is so rapid that it cannot be controlled to effect a partial closure of the blades. Partial closure of the scissor blades is frequently necessary. For example, when an ophthalmic surgeon is cutting the retinal membrane, one of the blades must be gradually inserted or "teased" under the membrane without damaging the underlying tissue, and the blades must be closed and opened gradually to prevent irreversible trauma to the retinal tissue. The pneumatically driven cutting instruments known in the prior art cannot perform this delicate procedure, as each pneumatic pulse causes the blades to close rapidly and completely and chop the tissue therebetween.

To overcome this deficiency in the pneumatically driven instruments, other automatic scissors arrangements have been devised using, e.g., a stepper motor coupled to a threaded member to close and open the scissor blades with greater proportional control. These devices suffer from poor control of the handpiece, due to the gyroscopic precessional force exerted by the rapidly rotating motor. Other devices use a cable-in-sleeve arrangement to operate the blades from a distant motive source. These instruments are imprecise, in that repositioning and other movement of the handpiece may alter the relationship of the cable and sleeve and cause unforeseen and undesirable closure of the blades. Thus there is no known power-operated surgical device in the prior art which is designed to perform gradual cutting, termed proportional cutting.

SUMMARY OF THE PRESENT INVENTION

The present invention generally comprises a system for operating a pneumatic scissors or microscissors to achieve proportional cutting. The system for proportional control of a pneumatic cutting device includes a linear solenoid valve having a flow rate therethrough proportional to the current passing through the solenoid. The linear solenoid valve is actuated by a selectively varied electrical signal generated by a potentiometer or the like operated by a pedal foot controller. Regulated fluid pressure is fed through the linear solenoid valve to a pneumatic cutting device such as an intraocular microscissors which closes increasingly as the applied pressure increases. The linear solenoid valve includes a flow path which is variably constricted or closed by a valve member, and a solenoid which is arranged to pull the valve member to open the flow path. An elastic member is disposed to resiliently bias the valve member to the closed position; the linear restoring force of the elastic member provides a generally linear relationship between the fluid flow-through rate and the current through the solenoid, and a proportional relationship between the control pedal position and closure of the cutting device.

BRIEF DESCRIPTION OF THE DRAWINGS

FIG. 1 is a functional block diagram of the system of the present invention for driving a pneumatic cutting device in a proportional cutting mode.

FIG. 2 is a cross-sectional elevation of the linear solenoid valve of the present invention.

FIG. 3 is a schematic representation of the linear solenoid valve of the present invention.

DESCRIPTION OF THE PREFERRED EMBODIMENT

The present invention generally comprises a pneumatic system 10 for driving a pneumatically operated cutting instrument in a proportional cutting mode. It may be used with a wide range of pneumatic cutting instruments, and in particular ophthalmic surgical devices. One such device is an intraocular microscissors, manufactured by Greishaber, Inc. of Switzerland, although the present invention is not limited to this instrument.

A salient feature of the present invention is the provision of a linear solenoid valve. With regard to FIGS. 2 and 3, the construction of the linear solenoid valve 11 includes a solenoid coil 32 wound about a hollow tubular member 33. One end of the tubular member 33 is sealed by a plug 34, and the stem of a valve member 36 is slidably received in the other end portion of the member 33. A significant feature of the invention is the provision of an elastic member 35 disposed between the plug 34 and the valve stem 36 to bias the latter member outwardly of the tube 33. The member 35 may comprise elastomeric rubber, foamed plastic, or the like, and it exhibits a restoring force which varies linearly with the amount of compression applied thereto.

A valve head member 37 is secured at the open end of the tube 33, and includes a valve seat 38 adapted to receive the distal end of the valve stem 36. A collar 39 is secured to the member 37 by threads, and an O-ring seal 21 retains pressure in the assembly. A valve port member 22 is joined to the collar, and includes an inlet port 23 and an outlet port 24. The flow path between the inlet and outlet includes an orifice 26 which is selectively and variably opened by axial translation of the valve member 36. The magnetic force generated by the solenoid coil 32 drives the valve stem 36 toward the plug 34, thus opening the orifice 26. However, this translation is opposed by the linear restoring force of the elastic member 35, so that an incremental increase in the fluid flow through the orifice 26 requires an incremental increase in the magnetic force driving the valve stem and thus in the current fed through the coil 32. The elastic member also provides a damping effect to the motion of the valve stem, and thus is superior to a metal spring or the like. The material of the elastic member is generally serviceable through approximately one billion operating cycles.

The linear solenoid valve is supplied with pressurized fluid from a pressure regulator 12 connected to the input port 23. The output port is connected to a pneumatic cutting device, such as a pneumatic scissors 13. The solenoid coil 32 is electrically powered by a direct current signal provided by a variable power supply 18 controlled by a potentiometer 14. A foot controller 16 is also provided, with the pedal 17 thereof connected in actuating fashion to the wiper of the potentiometer. That is, the angular position of the pedal 17 determines the voltage applied to the coil 32, and thus the current passing through the coil. As the pedal is increasingly depressed, the current increases and the solenoid increases the opening of the valve. Likewise, when the pedal is released to return upwardly, the current decreases and the solenoid permits the valve member 36 to translate toward the port 26 to further restrict the flow therethrough.

It may be appreciated that as the valve opening increases, the pressure applied to the scissors 13 increases, causing the scissor blades to decrease the angle therebetween and close on any tissue disposed therebetween. Thus pressing down on the pedal 17 drives the blades to close in accordance with the amount of angular excursion of the pedal. As a result, proportional cutting using the pneumatic scissors is easily achieved. Repeated cycling of the scissors may be accomplished by repeatedly depressing and releasing the pedal.

It should be noted that other types of controllers may be used in place of the pedal controller 16, and that other variable voltage sources may be employed in place of the potentiometer 14, without departing form the present invention.

We claim:

1. A proportional cut controller for a pneumatically driven ophthalmic micro-surgical cutting device having cutting means operatively connected to and having all cutting movement corresponding to a means which is moveably responsive to increases or decreases in pressurized fluid exerted upon it from a pressurized fluid source comprising:
   a proportional solenoid valve means for regulating the flow of pressurized fluid between said pressurized fluid source and said cutting device in order to control the movement of said cutting means of said cutting device; said solenoid valve means including a valve port through which the pressurized fluid flows, a valve stem to selectively vary the flow of pressurized fluid through said valve port, an elastic member disposed to bias said valve stem to a closed position over said valve port, and a solenoid means for urging said valve stem against said elastic member to open said valve port by moving said valve stem away from said valve port by varying distances;
   means for driving said solenoid means of said solenoid valve means, said means including a variable electrical signal selected and produced by an adjustable control element, with the flow of pressurized fluid through said valve being determined by the distance said valve stem is moved away from said valve seat which is controlled by and proportional to said variable electrical signal, and the cutting action in all directions of said cutting means of said cutting device being proportional to said variable electrical signal produced by the control element.

2. The controller of claim 1 wherein said elastic member includes a restoring force which varies linearly with the amount of compression applied to it, said force opposes translation of the valve stem away from the valve port.

3. The controller of claim 2 wherein the elastic member provides a damping effect to the motion of the valve stem.

4. A system for driving a pneumatically driven ophthalmic microsurgical cutting device having cutting means operatively connected to and having a proportional cutting mode corresponding to the movement of a means which is responsive to increases or decreases in pressurized fluid exerted on it from a pressurized fluid source, comprising:
   a proportional solenoid valve;
   a source of pressurized fluid connected through said proportional solenoid valve to the pneumatically operated cutting device;
   electrical means for driving the solenoid of said valve, including a variable voltage signal source, so that the fluid through said valve is proportional to said variable voltage signal and the cutting action in all directions of said cutting means in said proportional cutting mode is proportional to said variable voltage signal produced by the control means.

5. The system of claim 4, wherein said variable voltage signal source includes control means having a movable control element, and said variable voltage signal is proportional to the position of said movable control element.

6. The system of claim 5 wherein said control means comprises a pedal controller, and said movable control element comprises the pedal of said pedal controller.

7. The system of claim 4 wherein said cutting device comprises a pneumatically driven scissors.

8. The system of claim 7 wherein said variable voltage source signal source includes a control device having a movable control element which varies said voltage signal in accordance with the position thereof, so that closure of said scissors is proportional to said position of said movable control element.

9. The system of claim 4 wherein said solenoid valve includes a valve port through which said fluid flows, a valve member disposed to selectively vary the fluid flow through said valve port, an elastic member disposed to resiliently bias said valve member to close said valve port, said solenoid being disposed to translate said valve member against said resilient bias to open said valve port.

10. The system of claim 9 wherein said elastic member is composed of an elastomeric rubber compound.

11. A method for providing proportional cutting control to a pneumatically operated ophthalmic microsurgical cutting device having cutting scissor blades which by control and selection of an operator of the device move between an opened position towards a closed position upon increasing pneumatic pressure, which stop movement upon maintenance of pneumatic pressure at a given rate and amount, and which move towards said opened position upon decreasing the pneumatic pressure, comprising the steps of:
   increasing pneumatic pressure to said cutting device at a desired rate and amount by operating an adjustable control means causing proportional opening of a variably adjustable aperture between a pneumatic pressure source and said cutting device to cause movement of said blades towards said closed position;

maintaining pressure to said cutting device at a desired rate and amount by operating said control means causing said aperture to be maintained at a desired opening to stop movement of said blades in any direction;

decreasing the pressure of said cutting device at a desired rate and amount by operating said control means causing proportional closing of said aperture to cause movement of said blades towards said opened position.

12. The method of claim 11 wherein the speed at which said blades open and close is proportional to the rate at which the size of said aperture is increased and decreased.

13. The method of claim 11 wherein the size of said aperture is varied by a manually operable control means having a normally open state corresponding to said normally open position of said blades, and a closed state corresponding to said closed position of said blades, and being movable between said normally open and closed states to proportionally control the opening and closing of said blades according to desire.

14. A proportional cutting control device for use with pneumatically driven ophthalmic micro-surgical scissors having blades which are normally biased in an opened position, and where the blades of the scissors move towards one another upon increasing pneumatic pressure and move away from one another upon decreasing pneumatic pressure, and stop movement upon stabilization and maintenance of pneumatic pressure, comprising:

a proportional solenoid valve operatively connected between the scissors and a regulated variable pneumatic pressure source, the solenoid valve including an adjustably sized aperture between its inlet and outlet ports, and a solenoid operatively connected to a variable power supply and associated with the aperture so that an increase in current to said solenoid causes an increase in the size of the aperture, a decrease in current to solenoid causes a decrease in the size of the aperture, and stabilization and maintenance of current to the solenoid maintains the size in the aperture;

an adjustable control means moveable along a plurality of positions between first and second positions whereby movement of the control means causes a change in current to the solenoid in the proportional solenoid valve, movement towards the first position causing an increase in the current, movement towards the second position causing a decrease in current, and no movement causin no change in current, movement of the control means being proportional to the size of the aperture which in turn is proportional to the movement of the blades of the cutting device.

* * * * *